United States Patent [19]

Melanson et al.

[11] Patent Number: 5,749,968
[45] Date of Patent: May 12, 1998

[54] DEVICE FOR PRIMING FOR IMPROVED ADHERENCE OF GELS TO SUBSTRATES

[75] Inventors: David A. Melanson, Hudson, N.H.; Marc Alan Levine, Sharon, Mass.; John C. Spiridigliozzi, Dedham, Mass.; Thomas S. Bromander, Andover, Mass.; Dean M. Pichon, Concord, Mass.; George Selecman, Marblehead, Mass.; David J. Nedder, Attleboro, Mass.

[73] Assignee: Focal, Inc., Lexington, Mass.

[21] Appl. No.: 472,745

[22] Filed: Jun. 7, 1995

Related U.S. Application Data

[63] Continuation-in-part of Ser. No. 410,037, Mar. 23, 1995, and Ser. No. 379,848, Jan. 27, 1995, Pat. No. 5,626,863, and Ser. No. 24,657, Mar. 1, 1993, Pat. No. 5,573,934.

[51] Int. Cl.$^6$ ...................................................... B05C 5/00
[52] U.S. Cl. .......................... 118/300; 604/181; 604/183; 604/184; 604/191; 606/214
[58] Field of Search ................................... 118/300, 302; 604/59, 68, 181, 183, 184, 191; 606/214

[56] References Cited

U.S. PATENT DOCUMENTS

| 3,223,083 | 12/1965 | Cobey | 606/214 |
|---|---|---|---|
| 3,438,374 | 4/1969 | Falb et al. | 128/334 |
| 3,552,986 | 1/1971 | Bassemir et al. | 117/12 |
| 3,749,084 | 7/1973 | Cucchiara | 128/2 F |
| 3,939,049 | 2/1976 | Ratner et al. | 204/159.13 |

(List continued on next page.)

FOREIGN PATENT DOCUMENTS

| 0370646 A2 | 5/1990 | European Pat. Off. |
| 0 635 276 A1 | 1/1995 | European Pat. Off. |
| 0634140 A1 | 1/1995 | European Pat. Off. |
| 2668060 A1 | 4/1992 | France |
| 4402590 A1 | 4/1994 | Germany |
| WO 93/16687 | 2/1993 | WIPO |
| WO 93/16687 | 9/1993 | WIPO |
| WO 93/17669 | 9/1993 | WIPO |
| WO 94/21324 | 9/1994 | WIPO |
| WO 96/29370 | 9/1996 | WIPO |

OTHER PUBLICATIONS

AN 88-003699 Abstract, Derwent Publications Ltd., Week 8801, Nov. 20, 1987.
AN 93-410853 Abstract, Derwent Publications Ltd., Week 9351, Nov. 22, 1993.
Dumanian, et al., "A New Photopolymerizable Blood Vessel Glue that Seals Human Vessel Anastomoses Without Augmenting Thrombogenicity," *Plastic and Reconstructive Surgery* 95:901 (1995).

(List continued on next page.)

*Primary Examiner*—Laura Edwards
*Attorney, Agent, or Firm*—Wolf, Greenfield & Sacks, P.C.

[57] ABSTRACT

An improved barrier or drug delivery system which is highly adherent to the surface to which it is applied is disclosed, along with methods for making the barrier. In the preferred embodiment, tissue is stained with a photoinitiator, then the polymer solution or gel having added thereto a defined amount of the same or a different photoinitator is applied to the tissue. On exposure to light, the resulting system polymerizes at the surface, giving excellent adherence, and also forms a gel in the rest of the applied volume. Thus a gel barrier of arbitrary thickness can be applied to a surface while maintaining high adherence at the interface. This process is referred to herein as "priming". The polymerizable barrier materials are highly useful for sealing tissue surfaces and junctions against leaks of fluids. In another embodiment, "priming" can be used to reliably adhere preformed barriers to tissue or other surfaces, or to adhere tissue surfaces to each other. A first surface and a barrier, or another surface, are prestained with initiator, and a thin layer of gellable monomer containing initiator is placed between them. Strong adhesion is obtained between the two surfaces on gelation of the monomer. In a similar fashion, tissue surfaces can be adhered to each other in repair of wounds and formation of anastomoses. Methods for use of nonphotochemical systems and combined chemical/photochemical systems are described.

29 Claims, 3 Drawing Sheets

U.S. PATENT DOCUMENTS

| | | | |
|---|---|---|---|
| 4,040,420 | 8/1977 | Speer | 128/218 M |
| 4,179,304 | 12/1979 | Rossomando | 106/177 |
| 4,511,478 | 4/1985 | Nowinski et al. | 210/691 |
| 4,673,395 | 6/1987 | Phillips | 604/191 |
| 4,741,872 | 5/1988 | De Luca et al. | 264/4.7 |
| 4,804,691 | 2/1989 | English et al. | 523/118 |
| 4,826,945 | 5/1989 | Cohn et al. | 528/76 |
| 4,938,763 | 7/1990 | Dunn et al. | 604/891.1 |
| 4,979,942 | 12/1990 | Wolf et al. | 604/83 |
| 4,997,722 | 3/1991 | Adler | 428/596 |
| 5,049,135 | 9/1991 | Davis | 604/181 |
| 5,100,992 | 3/1992 | Cohn et al. | 528/26 |
| 5,104,375 | 4/1992 | Wolf et al. | 604/56 |
| 5,137,800 | 8/1992 | Neckers et al. | 430/281 |
| 5,160,745 | 11/1992 | De Luca et al. | 424/487 |
| 5,173,301 | 12/1992 | Itoh et al. | 424/448 |
| 5,209,776 | 5/1993 | Bass et al. | 106/124 |
| 5,254,086 | 10/1993 | Palmer et al. | 604/181 |
| 5,312,333 | 5/1994 | Churinetz et al. | |
| 5,372,585 | 12/1994 | Tiefenbrun et al. | 604/59 |
| 5,376,079 | 12/1994 | Holm | 604/191 |
| 5,385,606 | 1/1995 | Kowanko | 106/124 |
| 5,403,626 | 4/1995 | Kim et al. | 427/519 |
| 5,410,016 | 4/1995 | Hubbell et al. | 528/354 |
| 5,443,481 | 8/1995 | Lee | 606/214 |
| 5,459,177 | 10/1995 | Miyakoshi et al. | |
| 5,540,677 | 7/1996 | Sinofsky . | |
| 5,552,452 | 9/1996 | Khadem et al. | |

OTHER PUBLICATIONS

Kobayashi, et al., "Water–curable and biodegradable prepolymers." *J. Biom. Mat. Res.* 25:1481–1494 (1991).

Sawhney, et al., "Optimization of photopolymerized bioerodible hydrogel properties of adhesion prevention." *J. Biomed. Mats. Res.* .

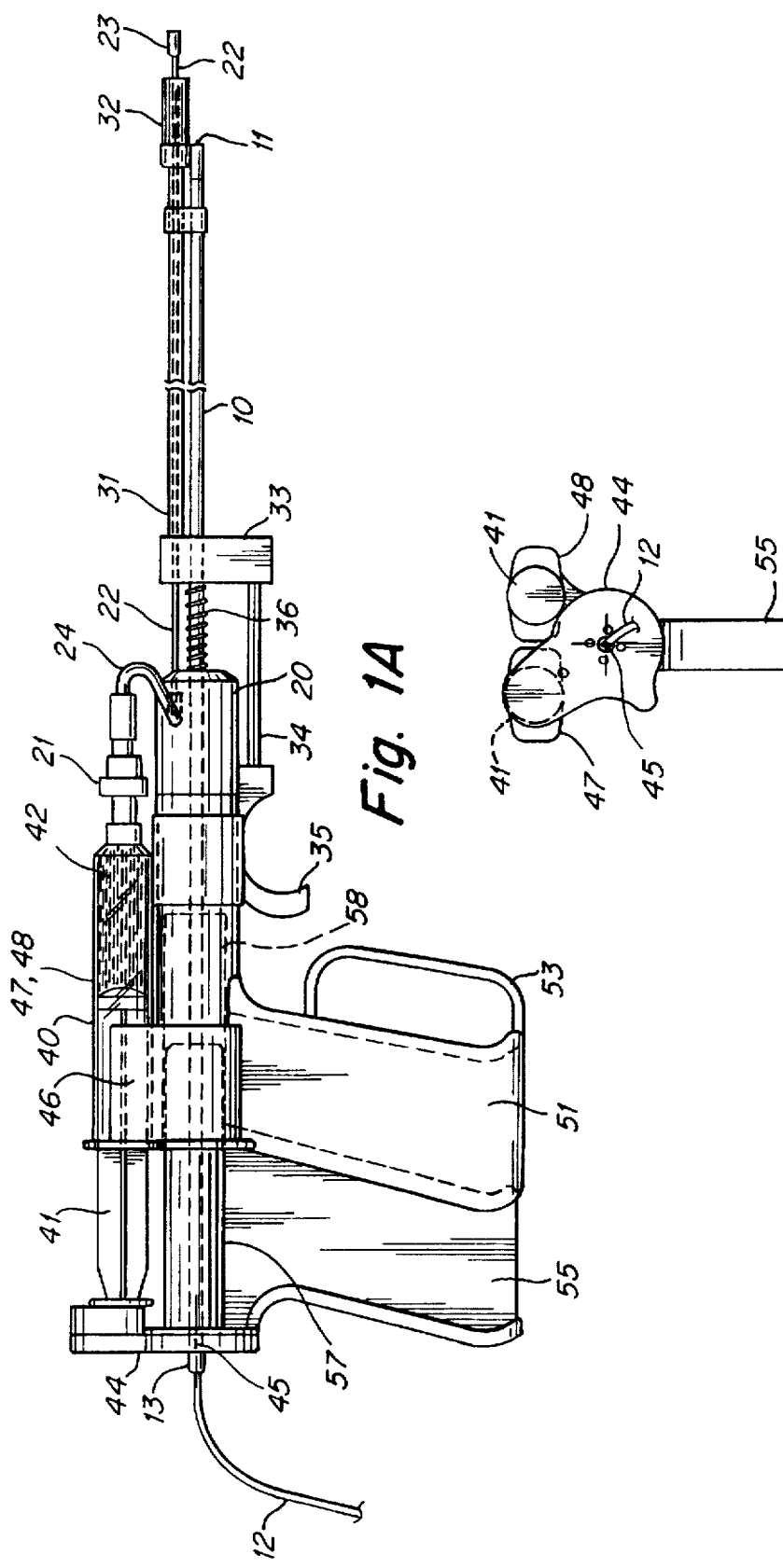
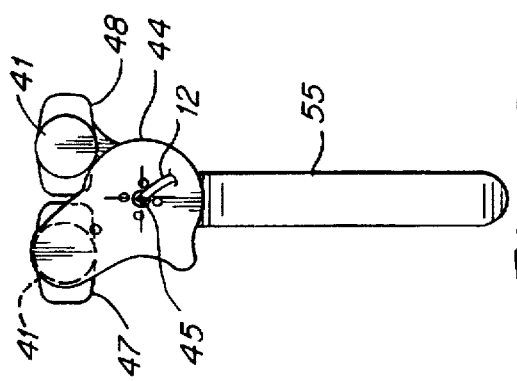
Fig. 1A
Fig. 1B

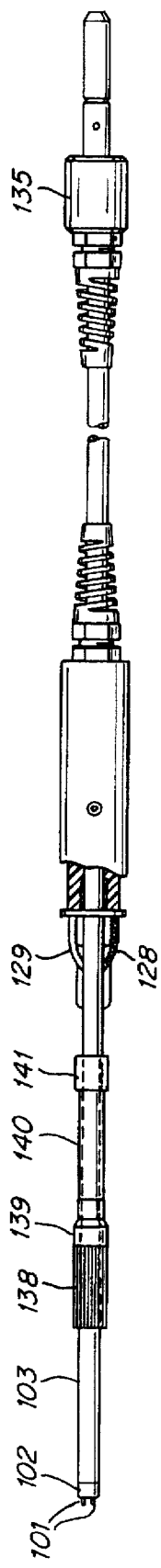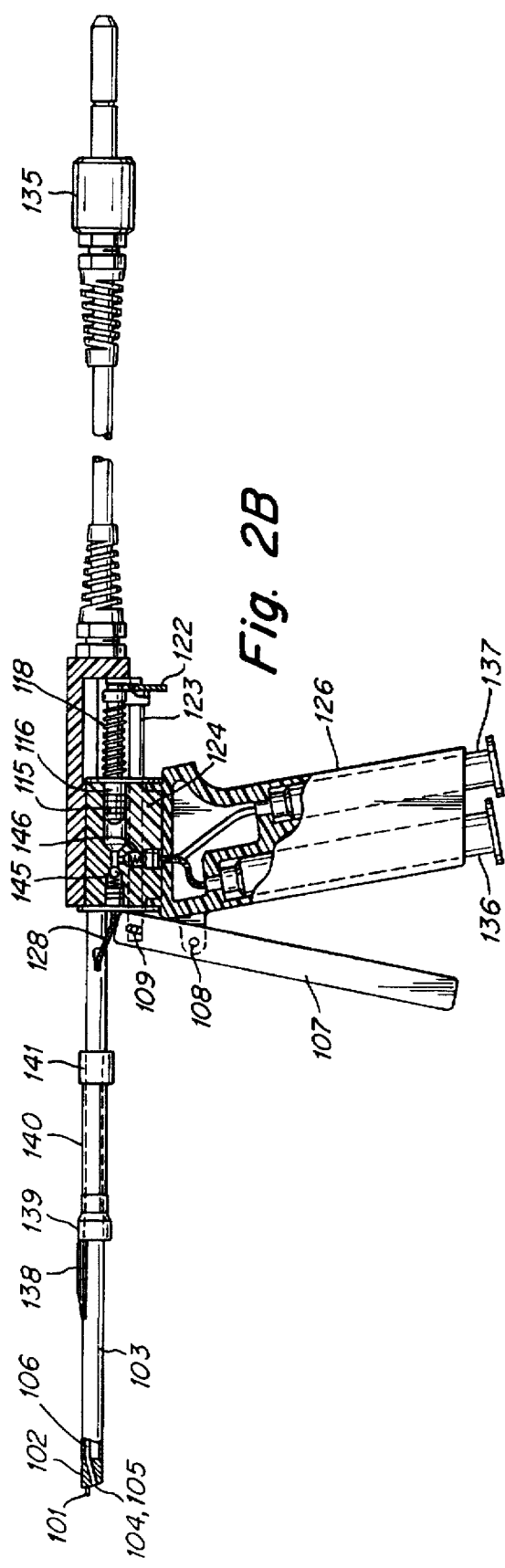

DEVICE FOR PRIMING FOR IMPROVED ADHERENCE OF GELS TO SUBSTRATES

This application is a continuation-in-part of U.S. Ser. No. 08/410,037 filed on Mar. 23, 1995 entitled "Initiator Priming For Improved Adherence of Gels to Substrates", by David A. Melanson, Amarpreet S. Sawhney, Marc A. Levine, John C. Spiridigliozzi, and Thomas S. Bromander; and a continuation-in-part of U.S. Ser. No. 08/379,848 filed on Jan. 27, 1995 now U.S. Pat. No. 5,626,863 and U.S. Ser. No. 08/024,657 now U.S. Pat. No. 5,573,934 Mar. 1, 1993.

BACKGROUND OF THE INVENTION

The present invention relates to methods and compositions for improving the adherence of polymer gels to surfaces, especially tissue surfaces; devices for applying the compositions and gels; and general methods for sealing surfaces with gels for therapeutic benefit.

Locally polymerized gels have been used as barriers and drug delivery devices for several medical conditions. Adherence of the formed gel to the tissue can be a problem, especially under surgical conditions, where the tissue surface to be treated is typically wet, and may further be covered with blood, mucus or other secretions. Hubbell and co-workers have described two methods for photopolymerizing gels in contact with tissue surfaces. In U.S. Pat. No. 5,410,016, hereby incorporated by reference, application of biodegradable macromers to tissue, followed by photopolymerization to form a gel, is described. Two methods for photopolymerizing gels are described. In "bulk" polymerization, a suitable photoinitiator and accessory reagents are solubilized or dispersed in a solution of gelling macromers. On application of light, the entire solution volume crosslinks to form a gel which acts as a local barrier or drug depot. These gels have substantial adherence to most surfaces, including tissue surfaces which are merely moist. However, if a confounding layer of fluid is present on the surface when the macromer/initiator solution is applied, then the gel may delaminate from the surface after its formation.

As also described in U.S. Ser. No. 08/024,657, which is hereby incorporated by reference, is an alternative way of form a gel layer on a surface, called the "interfacial" method. In this method, the surface to be coated is treated with a photoinitiator which adsorbs or absorbs to the surface. After washing away excess, unabsorbed photoinitiator, a polymerizable macromer solution is applied to the surface. On exposure to light, polymerization is initiated at the surface, and progresses outward into the solution to the limit of diffusion of the photoinitiator-generated radicals during their lifespan. Coating thicknesses of up to about 500 micrometers (microns) are routinely obtained. Since they are in effect "grown" from the tissue surface, such gel layers have excellent adhesion to the tissue surface under difficult conditions, including the presence of thin layers of fluid adherent to the surface. The limited thickness of such interfacial gels is desirable in some circumstances, but represents a major limitation where gels of substantially greater thickness than 500 microns are required, for example, for use in drug delivery, or in forming an effective barrier between the tissue surface and its surroundings.

In addition to the photopolymerizable gels described by Hubbell et al (WO 93/17669) and Sawhney et al, (*J. Biomed. Mats. Res.* 28, 831–838, 1994), systems for forming drug delivery depots or barriers on surfaces include the polymers described in U.S. Pat. No. 4,938,763 to Dunn, et al., U.S. Pat. Nos. 5,100,992 and 4,826,945 to Cohn et al, U.S. Pat. Nos. 4,741,872 and 5,160,745 to De Luca et al, and U.S. Pat. No. 4,511,478 to Nowinski et al. Use of preformed barrier materials such as Goretex™ membrane (W. L. Gore) has been described in the literature.

All of these materials are suitable for application to tissue and other substrates, although adhesion is in many cases limited, or in the case of the preformed barrier materials, essentially non-existent.

It is therefore an object of the present invention to provide methods and compositions for enhancing the adhesion of polymeric materials to tissue surfaces and other substrates.

It is a further object of the present invention to provide methods and compositions for increasing the thicknesses of polymeric materials which can be "tethered" to a tissue surface or other substrates.

It is a further object of the present invention to provide improved initiator systems for the formation of gels on tissues and other surfaces.

It is a further object of the present invention to provide improved methods and new medical indications for the sealing and coating of tissue.

It is a further object of the present invention to provide devices suitable for performing these operations.

SUMMARY OF THE INVENTION

An improved barrier, coating or drug delivery system which is highly adherent to the surface to which it is applied is disclosed, along with methods for making the barrier. In the preferred embodiment, tissue is stained with a photoinitiator, then the polymer solution or gel in combination with a defined amount of the same or a different photoinitator is applied to the tissue. On exposure to light, the resulting system polymerizes at the surface, giving excellent adherence, and also forms a gel throughout the illuminated volume. Thus a gel barrier or coating of arbitrary thickness can be applied to a surface while maintaining high adherence at the interface. This process is referred to herein as "priming". The polymerizable barrier materials are highly useful for sealing tissue surfaces and junctions against leaks of fluids. In the examples described below, the fluid is air; however, the principle is also applicable to other fluids, including blood, bowel contents, urine, and other fluids whose migration within a living organism must be contained.

In another embodiment, "priming" can be used to reliably adhere preformed barriers or coatings to tissue or other surfaces, or to adhere tissue surfaces to each other. A first surface and a preformed barrier or coating, or another surface, are prestained with initiator, and a thin layer of polymerizable monomer containing initiator is placed between them. Strong adhesion is obtained between the two surfaces on polymerization of the monomer. In a similar fashion, tissue surfaces can be adhered to each other in repair of wounds and formation of anastomoses.

The priming method is suitable for any mode of polymerization. While especially effective in photopolymerization, chemical or thermal polymerization can also be accomplished by this method. Further, an enhancement of photoinitiation can be achieved by adding suitable redox initiation components to the system, providing a new form of light-controlled chemically accelerated polymerization reaction, especially effective in the presence of blood.

BRIEF DESCRIPTION OF THE DRAWINGS

FIGS. 1*a* and 1*b* are schematic drawings of a two-fluid-one-dispenser version of an application device, in which FIG. 1a is a longitudinal schematic cross-section and FIG. 1b is a view from the proximal end of the device.

FIG. 2 is a schematic drawing of an alternate embodiment of a delivery device.

DETAILED DESCRIPTION OF THE INVENTION

Figure 3:
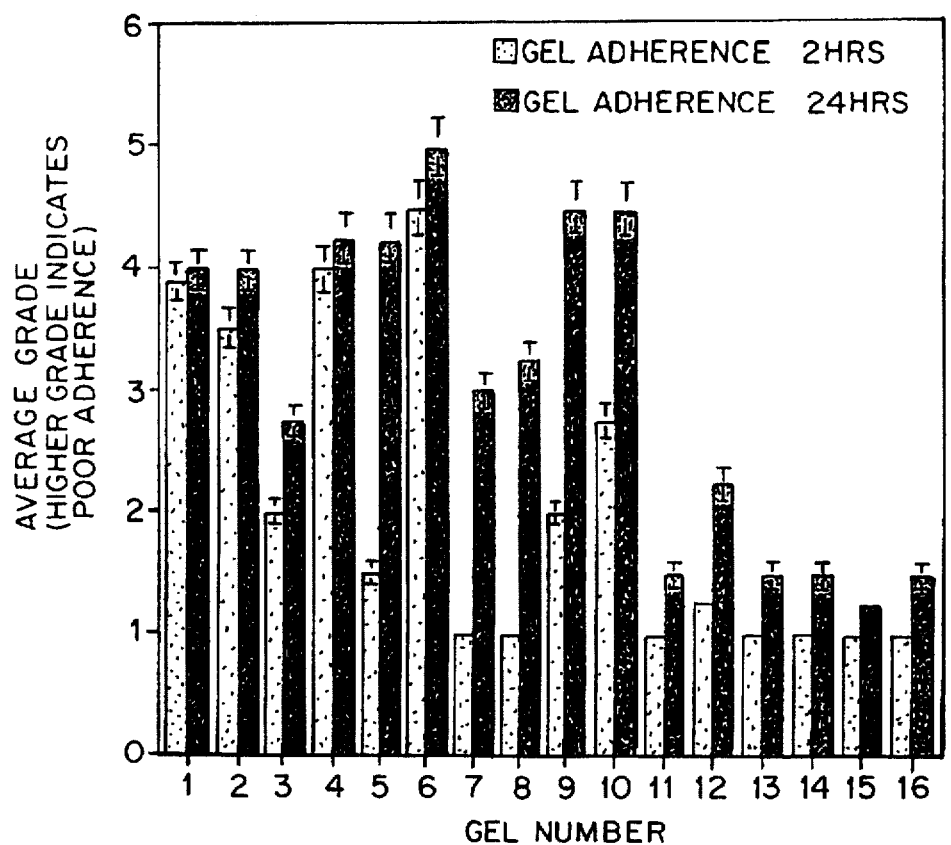
FIG. 3 is a graph of the relative adherence to tissue of several formulations, on a scale where a higher score indicates poorer adherence.

As described herein, one or more initiators are applied to a surface to form an absorbed layer. "Absorbed" is used herein to encompass both "absorbed" and "adsorbed". A solution of polymerizable molecules, referred to herein as "monomers", is then applied.

Methods

There are several embodiments of the method described herein.

In its simplest embodiment, one or more initiators or components of an initiation system are applied directly to the surface, and the unabsorbed excess is optionally removed by washing or blotting. The initiator solution may further contain one or more polymerizable monomers, and other useful formulating ingredients, including accelerators, co-initiators, sensitizers, and co-monomers. Then a liquid containing polymerizable monomers in combination with one or more initiators or components of an initiation system, which may be the same as or different from that absorbed in the first step, is applied. The system, if not self-polymerizing, is then stimulated to polymerize, for example by application of an appropriate wavelength of light.

The priming and monomer-application steps can also be combined. For example, if excess initiator is not removed before monomer addition, then subsequent application of monomer will result in mixture of initiator into the monomer layer. Similarly, if the monomer layer contains an initiator with a high affinity for the surface, then it is possible to apply a monomer layer containing initiator, and wait an appropriate time to allow preferential absorption of the initiator to the surface, to achieve the same effect.

All of these methods may collectively be described as application of the monomer in an "initiating-incorporating manner", encompassing any means of application and mixing which results in both an absorbed layer of initiator, and a layer of monomer incorporating an initiator, being present on a surface to be coated.

The initiators may be chemical, photochemical, or a combination thereof. With non-photochemical systems, a reductant component and an oxidant component may be present in the two parts of the solution, i.e., in the priming layer and the coating layer.

Alternatively, a two-step process can be used to form polymers, especially bioabsorbable hydrogels on tissue. In the first step the tissue is treated with an initiator or a part of an initiator system for the polymerization of olefinic (e.g. acrylic) or other functional monomers, optionally with monomer in the priming solution. This provides an activated tissue surface. In the second step, monomer(s) and, if appropriate, the remainder of an initiator system, are together placed in contact with the activated tissue, resulting in polymerization on the tissue. An example of such a system is the combination of a peroxygen compound in one part, and a reactive ion, such as a transition metal, in another.

This process of spontaneous polymerization does not require the use of a separate energy source. Moreover, since the process of polymerization is initiated when part one contacts part two, there are no "pot life" issues due to initiation of polymerization. If desired, part one or part two can contain dyes or other means for visualizing the hydrogel coating.

An example of a system that can he used in this method is the spontaneous "contact" initiator systems such as those found in two part "acrylic structural adhesives". All components of the materials used as described herein, however, must display biocompatibility as well as the ability to spontaneously polymerize on tissue. The use of tributyl borane for this purpose is illustrated here.

These systems can markedly simplify the delivery of gel to tissue, especially in areas hard to reach or hold for a photochemical system. The delivery system can be much simpler. Moreover, it has been discovered that a two-part chemical system such as a redox system and especially one based on peroxygen, can be used to chemically enhance the curing of a photochemical system, thereby combining the control of a photochemical system with the ability of a chemical system to overcome colored impurities, such as blood.

Compositions

MONOMERS

Any monomer capable of being polymerized to form a surface coating can be used. The monomers may he small molecules, such as acrylic acid or vinyl acetate; or they may be larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, U.S. Pat. Nos. 4,741,872 and 5,160,745 to De Luca et al., or U.S. Pat. No. 5,410,016 by Hubbell et al. Properties of the monomer, other than polymerizability, will be selected according to the use, using principles as known in the art. There is an extensive literature on the formulation of polymerizable coating materials for particular applications; these formulae can readily be adapted to use the improved adherence-promoting polymerization system described herein with little experimentation.

In the particular application area of coating of tissues, cells, medical devices, and capsules, formation of implants for drug delivery or as mechanical barriers or supports, and other biologically related uses, the general requirement of the coating materials are biocompatibility and lack of toxicity. For all biologically-related uses, toxicity must be low or absent in the finished state for externally coated non-living materials, and at all is stages for internally-applied materials. Biocompatibility, in the context of biologically-related uses, is the absence of stimulation of a severe, long-lived or escalating biological response to an implant or coating, and is distinguished from a mild, transient inflammation which accompanies implantation of essentially all foreign objects into a living organism.

The monomer solutions should not contain harmful or toxic solvents. Preferably, the monomers are substantially soluble in water to allow their application in a physiologically-compatible solution, such as buffered isotonic saline. Water-soluble coatings may form thin films, but more preferably form three-dimensional gels of controlled thickness.

It is especially preferable in cases involving implants that the coating formed be biodegradable, so that it does not have to be retrieved from the body. Biodegradability, in this context, is the predictable disintegration of an implant into small molecules which will be metabolized or excreted, under the conditions normally present in a living tissue.

Preferred monomers are the photopolymerizable, biodegradable, water-soluble macromers described by Hubbell et al in U.S. Ser. No. 08/022,687, now U.S. Pat. No. 5,410,016 the teachings of which are incorporated herein. These monomers are characterized by having at least two polymerizable groups, separated by at least one degradable region. When polymerized in water, they form coherent gels which persist until eliminated by self-degradation. In the most preferred embodiment, the macromer is formed with a core of a polymer which is water soluble and biocompatible, such as the polyalkylene oxide polyethylene glycol, flanked by hydroxy acids such as lactic acid, having coupled thereto acrylate groups. Preferred monomers, in addition to being biodegradable, biocompatible, and non-toxic, will also be at least somewhat elastic after polymerization or curing. Elasticity, or repeatable stretchability, is often exhibited by polymers with low modulus. Brittle polymers, including those formed by polymerization of cyanoacrylates, are not generally effective in contact with biological soft tissue.

It has been determined that monomers with longer distances between crosslinks are generally softer, more compliant, and more elastic. Thus, in the polymers of Hubbell, et al., increased length of the water-soluble segment, such as polyethylene glycol, tends to give more elastic gel, and these tend to adhere better, especially under stretching (as when applied to lung). Molecular weights in the range of 10,000 to 35,000 of polyethylene glycol are preferred for such applications, although ranges from 3,000 to 100,000 are useful.

In the discussion below and the examples, monomers of this kind, also called macromers, are often designated by a code of the form xxKZn. "xxK" represents the molecular weight of the backbone polymer, which is polyethylene glycol unless otherwise stated, in thousands of daltons. Z designates the biodegradable linkage, where L is for lactic acid, G is for glycolic acid, C is for caprolactone, and TMC is for trimethylenecarbonate. N is the average number of degradable groups in the block. The molecules are terminated with acrylic acid groups, unless otherwise stated; this is sometimes also indicated by the suffix A2.

INITIATORS

The term "initiator" is used herein in a broad sense, in that it is a composition which under appropriate conditions will result in the polymerization of a monomer. Compounds for initiation may be photoinitiators, chemical initiators, thermal initiators, photosensitizers, co-catalysts, chain transfer agents, and radical transfer agents. All initiators known in the art are potentially suitable for the practice of the priming technique. The critical property of an initiator is that the polymerization will not proceed at a useful rate without the presence of the initiator.

The "priming" initiator must adhere sufficiently to the surface to be coated to provide a local source of initiation of the reaction with the particular monomers to be applied. The initiator must also not be toxic when used in biologically-related applications, at least in the amounts applied. The initiator is preferably a photoinitiator. In discussing photoinitiators, a distinction may be drawn between photosensitizers and photoinitiators—the former absorb radiation efficiently, but do not initiate polymerization well unless the excitation is transferred to an effective initiator or carrier. Photoinitiators as referred to herein include both photosensitizers and photoinitiators, unless otherwise noted.

Photoinitiators provide important curing mechanisms for addition polymerization, and especially for curing of ethylenically-unsaturated compounds, such as vinylic and acrylic-based monomers. Any of the photoinitiators found in the art may be suitable, if they adhere to the particular surface. Examples of photo-oxidizable and photo-reducible dyes that may be used to initiate polymerization include acridine dyes, for example, acriblarine; thiazine dyes, for example, thionine; xanthine dyes, for example, rose Bengal; and phenazine dyes, for example, methylene blue. Other initiators include camphorquinones and acetophenone derivatives.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical which initiates polymerization. In an alternative mechanism, the initiator splits into radical-bearing fragments which initiate the reaction. Preferred dyes for use with these materials include eosin dye and initiators such as 2,2-dimethyl-2-phenylacetophenone, 2-methoxy-2-phenylacetophenone, Darocur™ 2959, Irgacure™ 651 and camphorquinone. Using such initiators, copolymers may be polymerized in situ by long wavelength ultraviolet light or by light of about 514 nm, for example.

A preferred photoinitiator for biological use is Eosin Y, which absorbs strongly to most tissue and is an efficient photoinitiator.

It is known in the art of photopolymerization to use a wavelength of light which is appropriate for the activation of a particular initiator. Light sources of particular wavelengths or bands are well-known.

Thermal polymerization initiator systems may also be used. Systems that are unstable at 37° C. and initiate free radical polymerization at physiological temperatures include, for example, potassium persulfate, with or without tetramethyl ethylenediamine; benzoyl peroxide, with or without triethanolamine; and ammonium persulfate with sodium bisulfite. Other peroxygen compounds include t-butyl peroxide, hydrogen peroxide and cumene peroxide. As described below, it is possible to markedly accelerate the rate of a redox polymerization by including metal ions in the solution, especially transition metal ions such as the ferrous ion. It is further shown below, that a catalysed redox reaction can be prepared so that the redox-catalysed polymerization is very slow, but can be speeded up dramatically by stimulation of a photoinitiator present in the solution.

A further class of initiators is provided by compounds sensitive to water, which form radicals in its presence. An example of such a material is tri-n-butyl borane, the use of which is described below.

CO-INITIATORS AND COMONOMERS

Any of the compounds typically used in the art as radical generators or co-initiators in photoinitiation may be used. These include co-catalyst or co-initiators such as amines, for example, triethanolamine, as well as other trialkyl amines and trialkylol amines; sulfur compounds; heterocycles, for example, imidazole; enolates; organometallics; and other compounds, such as N-phenyl glycine.

Co-monomers can also be used. They are especially useful when the monomer is a macromolecule, as in Example 1 below; in that case, any of the smaller acrylate, vinyl or allyl compounds can be used. Comonomers can also act as accelerators of the reaction, by their greater mobility, or by stabilizing radicals. Of particular interest are N-vinyl compounds, including N-vinyl pyrrolidone, N-vinyl acetamide, N-vinyl imidazole, N-vinyl caprolactam, and N-vinyl formamide.

SURFACTANTS, STABILIZER, AND PLASTICIZERS

Other compounds can be added to the initiator and/or monomer solutions. Surfactants may be included to stabilize any of the materials, either during storage or in a form reconstituted for application. Similarly, stabilizers which prevent premature polymerization may be included; typically, these are quinones, hydroquinones, or hindered phenols. Plasticizers may be included to control the mechanical properties of the final coatings. These are also well-known in the art, and include small molecules such as glycols and glycerol, and macromolecules such as polyethylene glycol.

DRUGS

Biologically active materials may be included in any of the coatings described herein, as ancillaries to a medical treatment (for example, antibiotics) or as the primary objective of a treatment (for example, a gene to be locally delivered). A variety of biologically active materials may be included, including passively-functioning materials such as hyaluronic acid, as well as active agents such as growth hormones. All of the common chemical classes of such agents are included: proteins (including enzymes, growth factors, hormones and antibodies), peptides, organic synthetic molecules, inorganic compounds, natural extracts, nucleic acids, lipids and steroids, carbohydrates, glycoproteins, and combinations thereof.

SURFACES TO BE TREATED

Surfaces to be coated include biologically-related surfaces of all kinds. In particular, any tissue or cell surface is contemplated, as well as the surface of a device to be used in the body or in contact with bodily fluids. A coating may be applied to the surface of any of these, in an amount effective to improve tenacity of adherence. Moreover, the technique may be used to adhere surfaces to each other. For example, wounds in living tissue may be bonded or sealed using this technique or preformed medical appliances may be bonded to tissue. Examples of such applications are grafts, such as vascular grafts; implants, such as heart valves, pacemakers, artificial corneas, and bone reinforcements; supporting materials, such as meshes used to seal or reconstruct openings; and other tissue-non-tissue interfaces. A particularly important class of tissue surfaces is those which are friable, and therefore will not support sutures well. Adherent coatings can seal the suture lines, support sutured areas against mechanical stress, or substitute entirely for sutures when mechanical stress is low. Examples of such situations include vascular anastomosis, nerve repair, repair of the cornea or the cochlea, and repair of the lung, liver, kidney and spleen.

The priming technique can also be used on non-tissue surfaces in general, where useful bonds may be formed between similar or dissimilar substances, and solid or gel coatings are tightly adhered to surfaces. In particular, a pre-formed gel, or other fragile material, may be tightly adhered to a supporting material by this method.

BIOLOGICALLY ACTIVE AGENTS

Biologically active substance can be incorporated into the polymer. Examples of useful biologically active substances include proteins (including enzymes, growth factors, hormones and antibodies), peptides, organic synthetic molecules including antibiotics, inorganic compounds, natural extracts, nucleic acids including genes, antisense nucleotides, and triplex forming agents, lipids and steroids, carbohydrates, including hyaluronic acid and heparin, glycoproteins, and combinations thereof.

Methods of Treatment

Generally, any medical condition which requires a coating or sealing layer may be treated by the methods described herein to produce a coating with better adherence. In the examples below, lung tissue is sealed against air leakage after surgery using the priming technique. Likewise, wounds may be closed; leakage of blood, serum, urine, cerebrospinal fluid, air, mucus, tears, bowel contents or other bodily fluids may be stopped or minimized; barriers may be applied to prevent post-surgical adhesions, including those of the pelvis and abdomen, pericardium, spinal cord and dura, tendon and tendon sheath. The technique may also be useful for treating exposed skin, in the repair or healing of incisions, abrasions, burns, inflammation, and other conditions requiring application of a coating to the outer surfaces of the body. The technique is also useful for applying coatings to other body surfaces, such as the interior of hollow organs, including blood vessels. The techniques can also be used for attaching cell-containing matrices, or cells, to tissues, such as meniscus or cartilage.

GENERAL SEALING OF BIOLOGICAL TISSUES

As shown in the examples below, the priming method of polymerization is especially effective in the sealing of biological tissues to prevent leakage. However, the examples also demonstrate that a degree of sealing can be achieved with photopolymerizable systems without the improvement of priming the tissue with photopolymerizing initiator. There have been numerous attempts to reliably seal tissue with a number of materials, including most prominently cyanoacrylates and fibrin glues. None of these prior art techniques has been entirely satisfactory. Cyanoacrylates, which polymerize on exposure to moisture, and can be accelerated by amines, are very "stiff" once polymerized. If there is any motion of the biological material, they tend to crack, and lose their self-cohesion and/or their adherence to tissue. Fibrin glues can be difficult to prepare, especially in the currently-preferred autologous version; they require enzymatic or toxic chemical means to be gelled or crosslinked; and they are rapidly degraded by native enzymes.

The range of uses of sealing or bonding materials in the body is very large, and encompasses many millions of potential uses each year. In cardiovascular surgery, uses for tissue sealants include bleeding from a vascular suture line; support of vascular graft attachment; enhancing preclotting of porous vascular grafts; stanching of diffuse nonspecific bleeding; anastomoses of cardiac arteries, especially in bypass surgery; support of heart valve replacement; sealing of patches to correct septal defects; bleeding after sternotomy; and arterial plugging. Collectively, these procedures are performed at a rate of 1 to 2 million annually. In other thoracic surgery, uses include sealing of bronchopleural fistulas, reduction of mediastinal bleeding, sealing of esophageal anastomoses, and sealing of pulmonary staple or suture lines. In neurosurgery, uses include dural repairs, microvascular surgery, and peripheral nerve repair. In general surgery, uses include bowel anastomoses, liver resection, biliary duct repair, pancreatic surgery, lymph node resection, reduction of seroma and hematoma formation, endoscopy-induced bleeding, plugging or sealing of trocar incisions, and repair in general trauma, especially in emergency procedures. In plastic surgery, uses include skin grafts, burns, debridement of eschars, and blepharoplasties (eyelid repair). In otorhinolaryngology (ENT), uses include nasal packing, ossicular chain reconstruction, vocal cord reconstruction and nasal repair. In opthalmology, uses include corneal laceration or ulceration, and retinal detachment. In orthopedic surgery, uses include tendon repair, bone repair, including filling of defects, and meniscus repairs. In gynecology/obstetrics, uses include treatment of myotomies, repair following adhesiolysis, and prevention of adhesions. In urology, sealing and repair of damaged ducts, and treatment after partial nephrectomy are potential uses. Sealing can also be of use in stopping diffuse bleeding in any of a variety of situations, including especially treatment of hemophiliacs. In dental surgery, uses include treatment of periodontal disease and repair after tooth extraction. Repair of incisions made for laparoscopy or other endoscopic procedures, and of other openings made for surgical purposes, ate other uses. Similar uses can be made in veterinary procedures. In each case, appropriate biologically active components may be included in the sealing or bonding materials.

APPLICATION TECHNIQUES AND DEVICES

Both priming and polymer addition may be accomplished by simple dripping of material onto the surface to be coated. This can be accomplished using common devices such as a syringe, a pipet, or a hose, depending on scale. More uniform applications may be obtained using an applicator, such as a brush, a pad, a sponge, a cloth, or a spreading device such as a finger, a coating blade, a balloon, or a skimming device. These may further be used to rub the surface to improve penetration of the primer or the monomer, or to mix primer and monomer in situ on the surface. In large-scale applications, fluid layers may be applied with large-scale coating machinery, including roll coaters, curtain coaters, gravure and reverse gravure devices, and any of the coating devices known in the art. Sprayers may be used at any scale, especially for lower-viscosity primers or polymerizable monomer layers.

Application techniques and devices may be combined, as in applying fluid from a syringe, and then rubbing it into the surface with a finger tip. Such operations may be repeated, as in applying drops of priming initiator; rubbing these into the surface with a brush; repeating this operation; adding monomer solution; rubbing it in; and finally applying additional layers of monomer before or during the application of curing means, such as light, heat, or slow release of peroxide radicals.

An additional application means which is required in many coating techniques described herein, and in particular in the preferred coating method which uses photoinitiation to cure the monomer, is a light source. For large-scale application, flood lamps and similar devices are useful. In small, localized applications, such as tissue sealing and coating, it may he preferable to use a localized source such as a fiber optic or light guide, which can project radiation of the appropriate wavelength onto the site to be treated to cause polymerization of the monomer. Also, a light emitter could be carried on a device, as a miniature bulb. A focused beam from a remote source could be suitable if, for example, the surface was exposed. In exposed surfaces, it is possible that ambient light could be sufficient to polymerize the coating, especially at high initiator levels.

Each of the applications means can be separate, so that a kit of application means could contain, for example, one or more reservoirs, one or more pads or brushes, and if required at least one light guide. The application means could also be combined in whole or in part. For example, a dripping device, such as a tube, could be combined with a spreading device, such as a brush. These could further be combined with a is light guide. Such combination devices are especially desirable in treatment of living organisms, and especially humans, to maximize the simplicity of a procedure and the probability of correctly conducting it.

Thus, a combination device for conducting a primed photopolymerization in a biological or medical setting will contain at least the following elements:

a) one or more means for applying a fluid to a surface, selected from dripping means, irrigating means, spraying means, applicator pad means including brushes, balloons, fabrics and foams, and rigid surfaces, such as spatulas, for applying paste-like or highly viscous fluids;

b) one or more optional means for spreading or rubbing a fluid onto a surface, which may be brushes, pads, rigid or semi-rigid protuberances, and which may be the same or different as the fluid-application means;

c) one or more reservoirs, or connecting conduits for receiving the contents of reservoirs into the device, for a primer, a monomer solution, and/or a combination thereof;

d) light-delivery means, which may be a fiber optic, a light guide, a focused remote beam, or a locally-deployed light source, such as a miniature lamp;

e) a proximal end adapted to be held by the person administering the treatment, optionally further including means for selection among the one or more application means, spreading means, reservoir means, and light-delivery means (i.e., switching means); and f) a distal end or ends, optionally adapted to be sterilizable, from which the one or more fluids are dispensed.

Other options for the device include metering means for the fluids, so that a controlled amount may be dispensed, or a controlled pressure may be maintained; feedback devices, such as optical viewers and indicators of function; and interlocks to correctly sequence the application procedure, or to insure dispensing of the required amounts of initiator, monomer, and light or other polymerization stimulator.

Many devices and arrangements can he constructed that meet these requirements. One embodiment of such a device is illustrated in FIGS. 1a and 1b, in which FIG. 1a is a longitudinal schematic cross-section, and FIG. 1b is a view from the proximal end of a two-fluid-one-dispenser version.

In FIG. 1a, a main shaft 10, of which the distal end is shown, carries light from a remote light source (not shown) coupled into an optical fiber or fibers 12 passing into the shaft through a bushing or strain-relief member 13 at the proximal end of the device, and through the axis of the device to a distal emission element 11. The emission element contains appropriate optical elements to distribute the light onto the site where polymerization is to occur. These may be as simple as a window, but may include other arrangements known in the art to distribute the light, including diffusers, lenses or gratings, and collimating stops.

Syringes 47, 48 (see also FIG. 1b) with check valves 21 are provided for the delivery of fluids via a connector 24 through a bifurcation in the body is extension 20 to a fluid delivery conduit 22, the ends of which are shown. The fluid delivery conduit may have a specialized applicator tip 23, such as a spray nozzle, or may be smooth for simple delivery of fluid by dripping. The fluid delivery conduit is optionally surrounded by a slidable tube 31 carrying a spreading device 32, which is connected by a block 33 which slides on the main shaft 10. The sliding block 33 slides the telescoping tube 31 on the fluid delivery conduit 22. The block is connected by a connecting rod 34 to a trigger mechanism 35, which is used to slide the spreading device 32 either distally of the emission element 23, or proximately of it, depending on the step of the priming operation. The trigger 35 may also optionally be provided with spring tensioners 36 or latches or detents for controlling position (not illustrated).

A syringe barrel 40 containing a fluid to be delivered 42 is fitted with a plunger 41. The plunger is selectively contactable by a plunger driver 44, which may be rotated about the device axis 45 to drive either of the two syringes 47, 48 shown in FIG. 1b. The syringes are held on the device by a clamp 46.

The plunger driver 44 is connected to a freely sliding rod 57 which can slide into a recess 58 in the device under the influence of slidable hand grip 55, which slides into handle 51. A finger guard 53 is provided for convenience.

In operation, the device is used as follows. With the spreading device 32 retracted to the proximal position, the plunger driver 44 is positioned over the filled initiator (primer) syringe 47, and by compressing the slidable portion of the hand grip 55 into the handle 51, fluid is dripped from delivery conduit 22 onto the target area. Then the spreading device is moved to the distal position and is used, by movement of the device as a whole by the operator, to spread the initiator priming solution over the entire target area. Alternatively, the spreading device may be in the distal position during primer delivery, so that the fluid is distributed by it.

Next, the spreading device is optionally retracted, and the driver 44 is moved to drive syringe 48, which contains a solution with monomer, initiator, carrier amine, and other ingredients. The monomer solution is dripped onto the target region, the spreader is advanced, and the monomer is rubbed into and distributed on the surface. Optionally, the spreader is retracted and further monomer is applied to the surface, optionally with the aid of the spreader, to form a thicker coat. Alternatively, the spreader may be in the distal position throughout delivery, so that the fluid is distributed by it.

Finally, the spreader is retracted, and the light source is activated to deliver light to emission element 11 to polymerize the coating on the surface of the tissue. Optionally, further monomer solution can be delivered during the emission of light to build up additional thickness. For this reason, both the delivery tube 22 and the main shaft 10 are preferably opaque to the light being used. This is conveniently achieved by constructing these elements of metal, such as standard syringe needle tubing. If the monomer solution is sensitive to room light, then the monomer syringe 48 should also be shielded or made of opaque material, and the monomer delivery path elements 21, 24 and 20 should likewise be opaque to the radiation wavelengths which initiate polymerization in the particular monomer/initiator combination. The rest of the device is made of any suitable material, such as a medical grade plastic. The device as a whole, or particular parts thereof such as the fluid dispensing pathway or the spreader, may be disposable.

In another embodiment, not illustrated, the elements 44, 55, 57 and 58 are omitted. The syringe plungers 41 are then exposed, and are driven directly by thumb pressure.

In an alternative embodiment, an additional trigger may be provided to connect to means for delivering a controlled amount of fluid with each squeeze of the trigger. Suitable ratchet means are known in the art; one such means is disclosed in co-pending application U.S. Ser. No. 08/036, 128 now abandoned. In an alternative embodiment, separate fluid pathways may be provided for each of the two fluids. The separate pathways may be parallel or concentric. In the former case, separate spreading elements may be provided for each pathway.

An embodiment of a delivery device incorporating both of these features is shown in FIG. 2. The device operates similarly to the device in FIG. 1, but uses a pumping mechanism composed of two pairs of one-way check valves, of which one pair is shown as 145 and 146, to pull fluid for delivery out of disposable syringes 136, 137, mounted in the handle 126, and inject the fluid through tubing 128, 129 into parallel delivery ducts terminating at orifices 101. The pumping action is driven by a trigger 107 mounted on a pivot 108. The trigger is linked via a connecting dowel 109 and a push rod 123 to either of a pair of spring 118-loaded pistons 116 by a switchable plate 122, similar in operation to that shown in FIG. 1, which couples to either of the pistons. The pistons are mounted in a housing 124 and sealed with O-rings 115. For illumination, an optical fiber 106 emitting through a window 104 with a diffuser 105, is connected through the body of the device to an optical connector 135 which delivers light from a remote source. The orifices, window and diffuser are carried in an end cap 102. Other features illustrated are similar to the device of FIG. 1, and include a main shaft 103), brush 138, and sliding brush shaft 140 with handle 141, to which the brush is removably attached with shrink-wrap 139.

Advantages of the device of FIG. 2 are the ability to deliver a known volume with each stroke of the trigger, and ease of changing syringes 136, 137 for replenishing reagent supply if required. As illustrated, one of the fluid delivery paths 128 is constructed from black flexible tubing, to avoid exposure of reactive monomer to light before delivery.

PACKAGING

The materials for making the coating can be packaged in any convenient way, and may form a kit, alone or together with the application device. The reactive monomers are preferably stored separately from the initiator, unless they are co-lyophilized and stored in the dark, or otherwise maintained unreactive. A convenient way to package the materials is in three vials (or prefilled syringes), one of which contains concentrated initiator for priming, the second of which contains reconstitution fluid, and the third containing dry or lyophilized monomer. Dilute initiator is in the reconstitution fluid; stabilizers are in the monomer vial; and other ingredients may be in either vial, depending on chemical compatibility. If a drug is to be delivered in the coating, it may be in any of the vials, or in a separate container, depending on its stability and storage requirements.

It is also possible, for a more "manual" system, to package some or all of the chemical ingredients in pressurized spray cans for rapid delivery. If the monomer is of low enough viscosity, it can be delivered by this route. A kit might then contain a spray can of initiator; a spray can or dropper bottle of monomer, initiator and other ingredients; and an optional spreading or rubbing device. If the monomer and initiator system are designed to polymerize under the influence of natural or operating room light, possibly with the supplement of a chemical initiator or carrier such as a peroxygen compound, then the technique could be suitable for field hospital or veterinary situations.

EXAMPLES

Example 1

Relative adhesion of coating to primed and unprimed surfaces

Fresh pig lung was primed in one area with a solution of photoinitiator (Eosin Y, 1 mg/mL (1000 ppm) in normal saline) and in another area with normal saline (prior art control). Excess fluid was removed by blotting. About 0.5 mL of monomer solution was applied to each spot. The monomer was polyethylene glycol (35,000 Daltons) terminated with caprolactone (average of 3.3 caprolactone groups per polyethylene glycol molecule) and capped with acrylic acid, essentially as described in Hubbell et al. The monomer solution contained 15% monomer (w/w), 90 mM triethanolamine, 20 ppm (w/w) Eosin Y, and 5 microliters/ mL vinylpyrrolidone (v/v). The samples were irradiated with green light until cured (40 sec. at 100 mW/cm$^2$) into a firm, transparent gel. Initial adherence was seen in both primed and control spots, although the primed spots had better overall adherence.

The lung was connected to a pressure-controlled inflation apparatus, and subjected to chronic fatigue for 1 hour of pneumatic inflation pressures at 25 to 30 cm of water, in 6 second cycles. This was designed to simulate the effects of breathing. After the fatigue test, the primed gel spots were still adherent, but the control gel spots could easily be lifted from the lung surface with forceps. Thus, adhesion under chronic stress was better with priming before polymerization.

Example 2
Sealing of wedge resection of lung

In lung operations, it is common to make a "wedge resection" to remove diseased areas. A combination stapler/ cutter is used to simultaneously cut and staple along one side of the wedge to be removed, and is then used to staple and cut the other side so that a wedge-shaped piece of lung is removed, while the remaining lung is simultaneously stapled closed. Despite a high staple density, the staple lines are prone to leak air, which can produce severe complications in a patient undergoing such an operation.

Frozen-thawed pig lungs were wedge-resectioned, using a ProxiMate™ TLC 55 reloadable linear cutter/stapler (Ethicon; Somerville, N.J.). Every second staple was omitted from the outer staple lines in the cassette to reliably induce leaks. Lungs were inflated with air to a pressure of 40 cm H$_2$O, and leaks were observed by pushing the stapled area just under the surface of a water bath (similar to leak testing of an inner tube). Next, staple lines were primed with 1000 ppm Eosin Y, blotted, and treated with the macromer mixture of example 1 which was then cured as described.

In a standard test for durability, the lungs were inflated to 20 cm water pressure for 10 cycles, over a period of 1 minute, and then held for 30 seconds at 40 cm water. The primed and sealed lung sections showed no leaks, demonstrating the effectiveness of the priming system in sealing known leaks.

Finally, pressure was increased in the primed lungs to determine the maximum pressure before leakage. Small leaks were typically seen at 75 cm water or above.

Example 3
Lap/Shear Strength of Primed and Unprimed Bonds

Adhesion under shear of gel to rat skin was determined on an Instron™ apparatus using standard methods. The biological surface was rat back skin, freshly removed from euthanized animals. It was glued to a glass slide, and treated as described below. A casting chamber was positioned above the skin, which also contained a gauze mesh which protruded from the chamber. Monomer solution was injected into the chamber and polymerized. The chamber was removed, and the tensile strength of the bond was determined by shearing the lap between the glass slide and the gauze mesh in a standard load cell on the Instron.

Skin treatments included none (control); primed; primed and pre-coated with monomer solution by drip; and primed, pre-coated with monomer solution by drip, and rubbed or mixed with a brush. A monomer solution as in Example 1 was applied, except that the monomer, "8KL5", had a smaller PEG molecule (8000 D), and was extended with lactate groups rather than caprolactone groups. With unprimed skin, a different initiator, Irgacure™ 651 (Ciba Geigy), was also used in the gelling monomer mixture.

With the non-primed Irgacure® system, average load at failure for 6 to 8 samples ranged from 49 grams of force with low-intensity mixing of monomer onto the surface, to 84 to 274 g. with rubbing. Similar results were obtained with the Eosin catalysed system with no primer (146 g average, range 80–220). When the tissue was pre-primed with Eosin, and monomer solution was thoroughly mixed with a brush, the failure force increased to 325 g (range 220–420). Thus priming can quantitatively improve early adherence, in addition to its much larger improvement in adherence after flexing.

Example 4
Sealing of a bronchus

A bronchus was stapled and cut during lobectomy by the techniques described for wedge resectioning. The staple line was coated as described in example 2, likewise preventing or stopping air leaks.

Example 5
Sealing of a laceration

A laceration 2 mm deep by 2 cm long was made on an isolated lung with a scalpel; the scalpel was taped to control the depth of cut. The lung was tested and found to leak. The laceration was primed, filled with monomer solution containing initiator, and the monomer was photopolymerized. The leak was sealed by this procedure.

Example 6
Coating of a medical device

A length of polyurethane tubing extrusion used for catheter shafts was dipped into an aqueous solution containing 20 ppm eosin. Excess eosin was rinsed off with water. The primed tubing was dipped into a solution containing 10% monomer (type 8KL5, as in example 3), 90 mM triethanolamine, 5 ppm vinylpyrrolidone, and 20 ppm eosin. Excess monomer was allowed to drip off. The monomer layer on the tubing was then photopolymerized to form an adherent gel coating. The adherence was strong enough to survive sectioning of the tubing with a razor blade; photomicrography showed complete adherence of the gel to the tubing. As a prior art control, the shaft was not primed. After dipping the un-primed shaft into the same monomer solution, the coating on the shaft was photopolymerized. A gel was formed, but failed to adhere to the shaft, and fell off during handling.

Example 7
Priming for surface adherence

Two surfaces of Pebax™ polyeteramid were stained with 1000 ppm Eosin Y and rinsed. Polymerizable monomer solution (10% 8KL5 in water containing 20 ppm eosin) was placed between the surfaces, and the sandwich was exposed to green light. Gel formed in the interface and held the surfaces together. In a control experiment, in which the surfaces were not primed, polymerization of the monomer occurred but no significant adherence of the surfaces was found.

Example 8
Priming of surfaces

On exposure to 1000 ppm of Eosin Y, surfaces of Teflon™ fluoropolymer and of polyethylene were observed to stain significantly. When monomer was added to such surfaces, and allowed to stand briefly, gels were formed on illumination. Adherence seemed inferior to that obtained on polyurethane.

Example 9
Priming of Uterine Horn and Adherence of Gel Layers

A model system was established for placing of barriers on mammalian uteruses after operations. Freshly excised uterine horns from euthanized pigs were removed from a saline bath and treated with 1000 ppm Eosin. Controls were not primed. Polymerizable monomer solution as in Example 7 was applied to the primed and control areas. Adherence of gel layers to the primed areas was very firm, while gels on control areas could be dislodged.

Example 10
Water-sensitive initiation

It is known to use tributylborane as a water-sensitive initiator of bulk polymerization. In this example, it is shown that TBB can serve as an initiator in interfacial polymerization, and thus as a primer in the present invention.

1M tributylborane (TBB) solution in THF was purchased from Aldrich. Lyophilized 35KL4A2 reactive monomer containing triethanol amine and eosin was made in these laboratories. Polyethylene glycol 400 (PEG 400) was obtained from Union carbide). Of the lyophilized powder of 35KL4A2, 0.5 gram was dissolved in 9.5 grams of PEG 400. The mixture was warmed using a heat gun up to 40°–5° C. to facilitate dissolution. To this solution, 30 µL of vinyl pyrrolidinone were added as a comonomer.

Using a glass syringe, 2 ml TBB solution were transferred to a sprayer, of the type used with thin layer chromatography plates. A small amount of TBB solution was sprayed on a glass coverslip and the PEG 400 solution containing 35KL4A2 was applied on the TBB solution. An immediate polymerization of the solution was noticed. The polymerized film was insoluble in water indicating crosslinking.

Similar polymerization was carried out on pig lung tissue. A small amount of TBB solution was sprayed on approximately 3 cm$^2$ of lung tissue. A 35KL4A2 solution in PEG was applied on top of the TBB solution. A small amount of TBB solution was also sprayed on top of the monomer solution. A well adherent film of 35KL4A2 on lung tissue was noticed. The polymerized film was elastic and well adherent to the tissue.

In an alternative procedure, application of the TBB initiator to tissue may be followed by application of monomer solution containing a photoinitiator, such as 20 ppm eosin. Photopolymerization is then used to build a thick layer of gel onto the initiated priming layer. Good adherence is predicted.

Example 11
Combination of redox free radical initiation systems with photoinitiation and/or thermal free radical initiation systems for increased polymerization speed Previous visible light photopolymerization of Focal macromonomers uses the aqueous eosin Y/triethanolamine photoinitiation system. This reaction has been observed to generate peroxides when carried out in the presence of dissolved oxygen in the buffer. One may exploit these generated peroxides as an additional source of free radical initiators for polymerization using a Fenton-Haber-Weiss style reaction. In an effort to use these formed peroxides as polymerization initiators, ferrous ion in the form of ferrous sulfate was added to the eosin Y/triethanolamine buffer and used in the photopolymerization of Focal macromonomers. Using an indentation style hardness test, gel stiffness a function of illumination time was used as a measure of gel cure.

In an experiment to evaluate the effectiveness of 50 ppm ferrous ion on the gelation of the Focal macromonomer 8KL5, two buffers were prepared. The first buffer was prepared in deionized (DI) water using 90.4 mM triethanolamine (TEOA) and pH adjusting to 7.4 with 6N HCl. The second buffer was prepared similarly but with the addition of ferrous sulfate such that there would be approximately 50 ppm ferrous ion available. These buffers were used to prepare a 10% (w/v) 8KL5 gelling solution with 1 microliter of vinyl pyrrolidinone per ml of gelling solution added as a comonomer. These solutions were then divided into gelling samples and had 20 ppm of eosin Y added to them. These samples were then illuminated using an all lines Ar laser at a power of 100 mW/cm$^2$. All illumination timepoints were done in triplicate and kept dark until stiffness testing was performed. In comparing a 10% (w/v) Focal macromonomer gelling solution with and without 50 ppm of ferrous ion added, the gel with the added iron gave significantly more cured gels than did the gel without iron.

It is further believed that any free radical initiation system, especially aqueous ones, capable of generating soluble peroxides can be greatly enhanced by the addition of soluble metal ions capable of inducing the decomposition of the formed peroxides.

Example 12
Redox-accelerated curing ("dual cure") of primed systems

A redox-accelerated system was compared to a purely photoinitiated system for priming tissues. The accelerated system was found to be especially effective in the presence of blood, which attenuates the light used in photopolymerization. An acute rabbit lung model of sealing of air leaks was used. A thoracotomy was made under anesthesia in the intercostal space of the rabbit. Anesthesia was induced using an intramuscular injection of ketamine-acepromazine. The seventh rib was removed to facilitate access to the lungs, and the animal was maintained on assisted ventilation. A laceration, about 8 mm×2 mm, was made on each of the middle and lower lobes of the lung. Air and blood leaks were immediately apparent. Bleeding was tamponaded using a gauze sponge, and the site was then rinsed with saline. Some blood remained, and a slow ooze of blood and air leakage from the site was still persistent on ventilation.

Two formulations were compared. In the first formulation, the priming solution contained 500 ppm Eosin Y and 90 mM TEOA (triethanolamine) in WFI (water for injection), while the macromer solution contained 15% w/v macromer (type 35KL4), 20 ppm Eosin Y, 5 mg/ml vinylcaprolactam, and 90 mM TEOA in WFI.

The second formulation contained 500 ppm Eosin Y, 15% 35KL4, and 3 mg/ml ferrous gluconate in WFI in the primer, and the same macromer solution as in the first formulation, supplemented with 500 ppm t-butyl peroxide.

Application methods were the same for both formulations, and consisted of application of 1 ml primer with gentle brushing, followed by application of 0.5 ml macromer solution by brushing, and then illumination with blue-green light at 100 mW/(square centimeter) while dripping an additional 0.5 ml of macromer. Total illumination time was 40 sec. Gels were formed on the tissue by both treatments, and the air and blood leakages were sealed.

Acute adhesion of the gel to tissue was rated on a scale of 1 (poor) to 4 (excellent). The first formulation scored 1.5, and the second scored 3.5. A notable improvement in adherence of the gel to the living lungs was seen with the use of the dual cure system.

Example 13
Optimization of iron concentrations

The objective is to find a redox system which does not instantaneously gel the macromer, and which can also be cured by light. Various formulae were prepared, and their polymerization was studied.

A stock monomer solution (solution 1) contained 15% w/w "35KL4" macromer, lot 031395AL, in TEOA buffer (90 mM triethanolamine, neutralized to pH 7.4 with HCl, in water for injection), and 4000 ppm VC (vinylcaprolactam) and 20 ppm eosin Y (photoinitiator). The buffer was selected to be compatible with dissolved iron.

Iron-monomer solution (solution 2) contained in addition 20 mg/ml of ferrous gluconate, 5.8 mg/ml of fructose, and 18 mg/ml of sodium gluconate.

Peroxide primer (solution 3) contained: 500 ppm eosin in TEOA buffer, plus 5 microliter/ml of 10% tertiary butyl peroxide. An alternative priming solution (3b) contained in addition 10% 35KL4.

Serial dilutions of one volume of iron monomer with two volumes of stock monomer were made, and the gelation time, in the absence of high-intensity light, upon addition of 1 volume of priming solution (3) to two volumes of diluted iron monomer was determined. The stock iron monomer and the 1:3 dilution gelled very rapidly (1–2 seconds), and a 1:6 dilution gelled in 3–4 seconds. The 1:9 dilution gelled very slowly no rapid gelation, and partial gelation after 1 hour. Further dilutions (1:27, 1:81) did not gel for at least one hour.

The formulation with 1:9 dilution, containing about 2.2 mg/ml of ferrous gluconate, was tested for its ability to adhere to excised tissue, and to gel in the presence of blood. Acute adherence was obtained with 1:9 iron monomer solution when primed with the basic peroxide priming solution, but better adherence was found with monomer-containing priming solution (3b).

In solution, a mixture of monomer solution (0.3 ml) and normal primer (0.13 ml; without peroxide), which polymerized when exposed to intense argon laser light, would not gel after addition of 2 drops of blood (about 33 mg). However, a mixture of the same volumes of 1:9 iron monomer, primer 3b, and blood gelled in 5 seconds on exposure to the same light source. Omission of the Na gluconate and fructose did not significantly change the gel time. The mixed formulation (iron monomer, peroxide primer, and blood) could be held for three hours in amber glass at room temperature with only slight decrease in the gelling time on exposure to light.

Thus, the formulation is sufficiently stable and controllable under operating room conditions, so that a preparation could be reconstituted at the start of the operation, and the material would be useful and applicable to tissue throughout the operation.

Example 14
Adherence to tissue at varied concentrations of peroxide and iron

Areas of excised fresh or frozen-thawed pig lung were primed with a photoinitiator, and a gel formed on the spot by dripping of photoinitiator-containing monomer, using the devices of FIG. 1 or of FIG. 2. In contrast to the previous example, the iron (ferrous gluconate) was in the primer, and the peroxide in the monomer solution. Gels formed by illumination at peroxide concentrations ranging from 76 to 900 ppm, and iron concentrations ranging from 1500 to 5000 ppm, had at least moderate adherence to tissue after overnight incubations.

Example 15
Factorial Screening Experiment for Gel Adherence with respect to varying quantities of N-vinyl Pyrrolidone, macromonomer concentration and triethanolamine The purpose of this experiment was to examine the effects of varying amounts acrylic acid, n-vinyl pyrrolidone and triethanolamine in an effort to understand the interfacial polymerization process variables to get uniform adherent gel coating. The chemistry related variables which affect the photopolymerization and gel adherence qualities include Eosin concentration in tissue, monomer concentration, PEG diacrylate content, and acrylic acid. The factorial experimental design was to screen the statistical significance of the variables mentioned above, in terms of individual and interactive effects. Various combinations of acrylic acid, monomer concentration, triethanolamine and n-vinyl pyrrolidone were examined in terms of gel-tissue adherence as the response factor.

The experimental results of the factorial experiment outlined below were graded in accordance to the performance with respect to two tests:

(1) The first time point was the gel adherence at 2 hours, the grading being conducted on a scale of 1–5.

(2) The second time point was the gel adherence in response to low shear force on adherence at 24 hours, the grading being conducted on a scale of 1–5.

(3) Grading was conducted by a person who did not know the composition of the test materials.

Materials

Pig aorta tissue, cut into small sections. The aortic tissue should be preferably devoid of fatty deposits; CCD camera; dissecting materials; visible light source (514 nm); timer; scintillation counter and vials.

Procedure (1) As given in the factorial design, there were 16 experiments. 32 scintillation vials were marked in sets of duplicate, such as 1.1, 1.2, etc. Since there were 16 experiments, there were 32 vials in total.

(2) A stock solution of 10% acrylic acid was prepared in PBS. 2.50 μl of 10% acrylic acid was added to the vials that had 10 ppm of acrylic acid in the experimental design.

(3) Triethanolamine solution was prepared by measuring, by weight, 0.67 g triethanolamine: 400 μl of PBS. The solution was pH balanced to 7.4 by adjustment with 6N HCl solution.

(4) The required amounts of VP, triethanolamine, acrylic acid was mixed in 5 ml of PBS.

(5) The required amounts of macromonomer were mixed in, in accordance to the experiment. pH measurements was taken again, to ensure that the solutions were at pH 7.4.

(6) The pig aorta tissue was sectioned into small rectangular pieces. All sectioned pieces were chosen, such that the tissue surface was devoid of fatty deposits.

(7) 32 scintillation vials were prepared for the storage of the gelled tissue, by the placement of 5 mls of PBS solution in each one.

(8) A 1 mg/ml solution of Eosin in PBS was prepared.

(9) A piece of aortic tissue was placed flat upon a clean surface, and a swab dipped in the eosin solution was pressed upon a spot for exactly 10 sec. Another spot was prepared upon the tissue with the eosin dipped swab. The spotted tissue was rinsed in PBS. The tissue section was then grasped with sharp tweezers and placed in the rectangular 4-well glass slide chambers. The tissue should lie flat inside the chambers.

(10) 400 μl of the macromer solution were placed in the well, and the plate was placed exactly under the collimated beam of the fiber optic cable. The tissue was exposed for exactly 15 sec.

(11) The exposed tissue was grasped gently with tweezers and placed in the scintillation vial with 5 mls of PBS. The vials were placed inside the shaker for 2 hours to hydrate.

(12) After 2 hours, the gels were viewed through a microscope to view the gel adhering to the tissue surface. The tissues were graded for adherence, quality and shape on a scale of 1–5. The microscope was fitted with a SONY CCD Camera. The physical state of the gel can be viewed satisfactorily for grading from 1–5.

(13) After the examination, the vials were placed in the shaker for approximately 24 hours, to examine the effect of low shear rate on the interfacial gel.

(14) The gels were examined for gel adherence and quality on a scale of 1–5.

TABLE 1

| | | Experiments | | |
|---|---|---|---|---|
| Rows | Monomer Conc. | TEA con. (μl of 60% soln) | VP (μl) | Acrylic Acid |
| 1 | 10 | 5 | 1 | 0 |
| 2 | 10 | 5 | 1 | 10 |
| 3 | 10 | 5 | 3 | 0 |
| 4 | 10 | 5 | 3 | 10 |
| 5 | 10 | 20 | 1 | 0 |
| 6 | 10 | 20 | 1 | 10 |
| 7 | 10 | 20 | 3 | 0 |
| 8 | 10 | 20 | 3 | 10 |
| 9 | 23 | 5 | 1 | 0 |
| 10 | 23 | 5 | 1 | 10 |
| 11 | 23 | 5 | 3 | 0 |
| 12 | 23 | 5 | 3 | 10 |
| 13 | 23 | 20 | 1 | 0 |
| 14 | 23 | 20 | 1 | 10 |
| 15 | 23 | 20 | 3 | 0 |
| 16 | 23 | 20 | 3 | 10 |

(15) The gels were graded according to the following scale:

TABLE 2

| Gel Adherence Rating System | |
|---|---|
| GRADE | CRITERION |
| 1 | Intact |
| 2 | Some edges loosened but otherwise intact |
| 3 | 50% intact |
| 4 | gel only attached by some edges, otherwise not-adhered |
| 5 | Not adhered |

Observations

The adherence score is presented in FIG. 3, in which a higher score represents worse adherence, in contrast to previous examples.

A Factorial Statistical Analyses of the gel adherence scores with respect to the variables individually, and in interaction with the other variables (acrylic acid, triethanolamine, N-vinyl pyrrolidone, monomer concentration) was performed using a Statistical Modeling Package. P values closer to zero indicates the statistical significance (95% confidence interval). The p-values for all the variables and their interactive effects were determined.

It was found that the monomer concentration was the dominant influence and highly significant. The TEA concentration was also significant. Variation in VP and acrylate were not significant in these ranges.

Example 16

Further tests of influence of monomer concentration and initiator on adherence of gels to tissues Variations in tissue adherence of gels can also be seen in non-primed systems. As noted in U.S. Pat. No. 5,410,016 to Hubbell et al., and in Dumanian et al, Plastic & Reconst. Surg. 95(5), 901–07 (1995), tissue sealing and adherence may also be obtained without priming.

Adhesion strength was determined by testing the strength of a lap shear of gel, which was formed between a glass and a plastic slide. One slide was fixed; the other was connected by a string over a pulley, with a cup on the vertical end of the string. After formation of the gel, the cup was filled from a peristaltic pump, and the stress at which failure occurred was calculated from the weight of the partially-filled cup at failure.

As a standard, 150 microliters of a solution containing 23% monomer, type 8KL5, and 300 mg/ml of Irgacure™ initiator, was spread between the slides and polymerized. This produced a high level of adherence, as determined by force to failure. A low-adherence control was the same solution with 10% monomer.

The following variations did not improve adherence: coating each slide with 10 microliters of 10% monomer solution containing 3× or 10× the amount of initiator, followed by application of 140 microliters of 10% monomer and polymerization. Doubling the precoating to 20 microliters was also ineffective. However, precoating with 23% monomer, at normal initiator level, significantly improved overall adherence.

Further testing used bleeding in a cut liver as a test. In this situation, 23% monomer was much more effective than 10% monomer in stopping bleeding. It appears from these experiments that higher monomer concentrations intrinsically adhere to tissue better than lower concentrations, at least in the ranges tested.

Example 17

Redox interfacial primed system

It was demonstrated that non-photopolymerization techniques can produce gels adherent to tissue. Thinly-sliced ham was soaked in deionized water, and a 1 by 2 inch piece was folded in half and the outer edges were bonded together. First, 0.1 ml of solution A was applied to the joint (Solution A contained 10% monomer 8KL5, 0.3% hydrogen peroxide, and 0.3% NVMA (N-vinyl N-methyl acetamide)). Then 0.2 ml of Solution B was applied. (Solution B contained 30% 8KL5, 20 mg/ml Ferrous Ammonium Sulfate hexahydrate (Aldrich), 3% fructose, and 0.3% NVMA. Cure was instantaneous, and no discoloration of the gel occurred. The bond held during overnight soaking in distilled water.

Example 18

Sprayed redox system

Using the above solutions, and with monomer concentrations varying from 5% to 10% in solution A and 10% to 30% in solution B, primer (solution A) was sprayed on semivertical surfaces, followed by solution B. Surfaces were the palm of the experimenter's hand, and petri dishes. The spraying procedure caused some foaming, but gels were formed on all surfaces. Because of running of the solutions down the surfaces, gels were thicker at the bottom but present throughout. In a similar experiment, the monomer 8KTMC, containing trimethylenecarbonate biodegradable linkages between the polyethylene glycol and the acrylate cap, seemed to adhere somewhat better than the 8KL5.

Example 19
Comparison of peroxygen compounds

Reductant solutions contained 10% 8KL5 monomer and 8% by volume of a ferrous lactate solution, which itself contained 1% ferrous lactate and 12% fructose by weight in water. Oxidant solutions contained 10% 8KL5 monomer and a constant molar ratio of oxidizer, which was, per ml of macromer solution, 10 microliters 30% hydrogen peroxide; 8.8 microliters tert-butyl peroxide; 15.2 microliters cumene peroxide; or 0.02 g potassium persulfate. 0.5 ml of reductant was mixed with 0.25 ml oxidizer, and time to gelation was noted. With hydrogen peroxide, gelling was nearly instantaneous, while with the others there was a short delay—about 1 second—before gelation. Doubling the t-butyl peroxide concentration also produced nearly instantaneous gelling. Hydrogen peroxide produced more bubbles in the gel than the others; persulfate had almost no bubbles. The bubbles in hydrogen peroxide may come directly from the reactant, as the other compounds have different detailed mechanisms of radical formation.

Example 20
Effect of reducing sugars

Using the procedures of example 19, the concentration of ferrous ion was reduced to 50 ppm, and the fructose was omitted. At 100 ppm HOOH in the oxidizing solution, gel time was increased to 3 to 4 seconds, with both Fe-gluconate and Fe-lactate, but gels were yellow. Addition of 125 ppm ascorbic acid to the reducing solution prevented the formation of the yellow color.

Example 21
Sodium gluconate addition

It was found that raising the pH of the iron-peroxide system from 3.7 to 5.7 by addition of sodium gluconate had no effect on gelation time.

Example 22
Compatibility with ultraviolet photoinitiators

Solution A contained 1 g 8KL5, 0.4 ml of a ferrous lactate solution (containing 0.4 g ferrous lactate and 4.8 g of fructose in a final volume of 40 ml of distilled water), and 8.6 g of distilled water. Solution B contained 1 g of 8KL5, 0.1 ml of 30% hydrogen peroxide, and 8.9 g water. Drops of A were allowed to fall into a solution of B, resulting in drops of gel which gradually accumulated at the bottom of the solution. If solution B was supplemented with 4% by volume of a solution of 0.2 g of Irgacure™ 651 photoinitiator dissolved (with heating) in 4 ml of Tween™ 20 detergent, then after making bead droplets as before, the entire solution could be gelled by application of UV light. This demonstrates the compatibility of the redox and UV-curing systems. Moreover, it would be possible to make the redox-cured droplets from a monomer which would degrade either faster or slower than the continuous-phase gel, as desired, thereby potentially creating a macroporous gelled composite.

Example 23
Relative adherence of gels

Various gel formulas were compared in their ability to stick to domestic ham, versus their ability to adhere the fingers of the hand together. It was found that adherence of a formula to one type of surface was only weakly predictive, at best, of the adherence to the other. In another experiment, it was found that persulfate-catalysed gels are less adherent to tissue than comparable t-butyl peroxide gels, but are relatively more adherent to metal. Thus, the optimal formulation may well depend on what is to be coated with gel.

Example 24
Intra-pleural sealing

A source of morbidity in lungs is the formation of bullae, which are sacs formed by separation of the plerua from the lung parenchyma. As a model for possible repair of bullae, the pleura of a detached lung was repeatedly nicked to generate small air leaks. Then a solution containing 150 of 35KL18 macromer, 20 ppm of eosin, 5 milligrams/ml vinylcaprolactam, and 90 mM triethanolamine was injected between the pleura and parenchyma at the sites of the air leaks. The solution spread preferentially between the tissue layers, forming a blister-like structure. The area was transilluminated from the pleural side with blue-green light for 40 seconds. A flexible gel was obtained, and the air leaks were sealed.

A similar procedure could be applied to other layered tissues to stop leaks and effusion. Because the gel is confined within the tissue, adherence to tissue is not a primary concern. There are a number of anatomical structures having layered tissue structures suitable for this method of sealing a tissue against leakage. Such tissue layers include the meninges, including the dura, the pia mater and the arachnoid layer; the synovial spaces of the body including the visceral and pareital pleurae, the peritoneum, the pericardium, the synovia of the tendons and joints including the bursae, the renal capsule, and other serosae; and the dermis and epidermis. In each case, a relatively fragile structure can be sealed by injection of a polymerizable fluid between adjacent layers, followed by polymerization. Formation of a biodegradable, biocompatible gel layer by non-intrusive processes such as photopolymerization is especially desirable, because it minimizes trauma to the tissue.

Example 25
Sealing of an Injured Artery

In an anesthetized pig, a 1.5 cm lengthwise incision was made in a carotid artery. The incision was closed with interrupted sutures, so that blood seepage occurred. The injured area was rinsed with saline, and the blood was suctioned from the treatment zone. The treatment zone was primed with 1 mg/ml eosin in buffer (TEOA in ⅓ normal phosphate buffered saline). A macromer solution was applied with a small paintbrush to the treatment zone under illumination with blue-gree argon ion laser light. In a first artery, the macromer solution contained 15% 35KC3.3, 4 mg/ml N-vinylcaprolactam, and 20 ppm eosin. In a second artery, the macromer was type 35KL18, and the macromer solution has a paste-like consistency. Four applications (0.5 to 1.0 ml each) were required to seal all leaks. It was easier to build thickness with the paste-like monomer. The pig was held under anesthesia for an hour, and the injury sites were reexamined and found to be still sealed.

Modifications and variations of the present invention will be obvious to those skilled in the art. Such modifications and variations are intended to come within the scope of the appended claims.

We claim:

1. A combination device for conducting a primed photopolymerization treatment in a biological or medical setting comprising:

a shaft having a proximal end to be held by a person administering the treatment and a distal end from which one or more fluids are dispensed;

a first conduit fluidly connectable to a first reservoir containing a photoinitiator and fluidly connected to the distal end of the shaft;

a second conduit fluidly connectable to a second reservoir containing a monomer solution and fluidly connected to the distal end of the shaft; and near the distal end of the shaft, a source of electromagnetic radiation of a wavelength that causes activation of the photoinitiator.

2. The device of claim 1 wherein the source of electromagnetic radiation is selected from the group consisting of a fiber optic, a light guide, a focused remote beam, and a light emitter.

3. The device of claim 1 further comprising means for application of the one or more fluids, selected from the group consisting of dripping means, irrigating means, spraying means, applicator pad means, and rigid surfaces.

4. The device of claim 3 further comprising one or more means mounted at the distal end of the shaft for spreading or rubbing a fluid onto a surface in addition to the means for application of the one or more fluids.

5. The device of claim 1 comprising at least two reservoirs, at least one of which contains a priming solution comprising an initiator and a carrier therefor, and at least one of which contains a polymerizable coating solution comprising a polymerizable monomer, an initiator, and a suitable carrier.

6. A device as in claim 11 further comprising a first dispenser associated with a first reservoir containing a photoinitiator and a second dispenser associated with a second reservoir containing a monomer solution and a lever near the proximal end of the shaft-coupled to an actuator switchable between a first position in which the lever is operably linkable to the first dispenser and a second position in which the lever is operably linkable to the second dispenser.

7. A device as in claim 6, wherein the lever has freedom of movement between a first position and a second position, and wherein movement of the lever from the first position to the second position, when a first reservoir is carried by the device and the actuator is positioned in its first position, causes a set amount of a composition contained in the reservoir to be dispensed through a conduit to an applicator outlet.

8. A device as in claim 7, further comprising a ratchet mechanism operably linking the lever to the actuator.

9. A device as in claim 6, wherein the lever, when the actuator is in its first position, is not operably linkable to the second dispenser.

10. A device as in claim 6, wherein each of the first and second dispensers is a syringe plunger, and the actuator is a syringe plunger driver.

11. A device as in claim 1, constructed and arranged to deliver to a tissue surface, separately, a first composition from a first reservoir without delivering a second composition from a second reservoir.

12. A device as in claim 1, including a grippable member near the proximal end of the shaft, wherein the shaft extends distally from the grippable member.

13. A device as in claim 1, wherein the shaft is rigid.

14. A device as in claim 1, wherein the source of electromagnetic radiation is a light source.

15. A device as in claim 14, further comprising an optical fiber connecting a remote light source to the light source.

16. A device as in claim 15, wherein the light source comprises the terminal portion of the optical fiber.

17. A device as in claim 1, further comprising a switch near the proximal end of the shaft, operable by a user of the device, and movable between a first position allowing projection of electromagnetic radiation from the electromagnetic radiation source, and a second position preventing projection of electromagnetic radiation from the electromagnetic radiation source.

18. A device as in claim 1, further comprising a spray nozzle at the distal end of the shaft fluidly connected to at least the first conduit.

19. A device as in claim 1, wherein at least one of the first conduit and the second conduit is opaque.

20. A combination device for conducting a primed photopolymerization treatment in a biological or medical setting comprising:

a shaft having a proximal end to be held by a person administering the treatment and a distal end from which one or more fluids are dispensed;

a first composition reservoir, including a dispenser, connected to a first conduit and a second composition reservoirs, including a dispenser, connected to a second conduit, the composition reservoirs each containing a primer, a monomer solution, or a combination thereof, and the conduits each fluidly connected to the distal end of the shaft;

a lever at the proximal end of the shaft movable between a first position and a second position;

a composition dispensing mechanism having a first position operably linking the first composition reservoir dispenser with the lever and a second position operably linking the second composition reservoir dispenser with the lever;

means for selection among the first position of the dispensing mechanism and the second position of the dispensing mechanism, wherein the lever, when moved from its first position to its second position, dispenses contents of the composition reservoir with which it is operably linked via the dispensing mechanism, whereby the contents of the first and second composition reservoirs are dispensable independently from the distal end from the shaft; and a source of electromagnetic radiation near the distal end of the shaft.

21. A device as in claim 20, further comprising a switch near the proximal end of the shaft, operable by a user of the device, and movable between a first position allowing projection of electromagnetic radiation from the electromagnetic radiation source, and a second position preventing projection of electromagnetic radiation from the electromagnetic radiation source.

22. A device as in claim 21, wherein the source of electromagnetic radiation is a light source.

23. A device as in claim 22, further comprising an optical fiber connecting a remote light source to the light source near the distal end of the shaft.

24. A device as in claim 23, wherein the light source comprises the terminal portion of the optical fiber.

25. A device as in claim 20, at least one conduit being fluidly connected to a spray nozzle at the distal end of the shaft.

26. A device as in claim 20, wherein at least one of the first and second fluid conduits is opaque.

27. A device as in claim 20, wherein the lever, when moved from its first position to its second position, dispenses a set amount of the contents of the composition reservoir with which it is operably linked via the dispensing mechanism.

28. A device as in claim 27, further comprising a ratchet mechanism operably linking the lever to the dispensing mechanism.

29. A device as in claim 20, wherein at least one of the first composition reservoir and the second composition reservoir is a syringe.

* * * * *